US008052941B2

(12) United States Patent
Lee et al.

(10) Patent No.: US 8,052,941 B2
(45) Date of Patent: *Nov. 8, 2011

(54) PACKAGES, BIOCHIP KITS AND METHODS OF PACKAGING

(75) Inventors: June-Young Lee, Anyang-si (KR); Dong-Ho Lee, Seongnam-si (KR)

(73) Assignee: Samsung Electronics Co., Ltd. (KR)

( * ) Notice: Subject to any disclaimer, the term of this patent is extended or adjusted under 35 U.S.C. 154(b) by 688 days.

This patent is subject to a terminal disclaimer.

(21) Appl. No.: 12/217,169

(22) Filed: Jul. 2, 2008

(65) Prior Publication Data

US 2009/0018035 A1 Jan. 15, 2009

(30) Foreign Application Priority Data

Jul. 13, 2007 (KR) ........................ 10-2007-0070875

(51) Int. Cl.
*G01N 21/75* (2006.01)
*C12M 1/34* (2006.01)
*B65B 7/00* (2006.01)

(52) U.S. Cl. ........................ 422/424; 435/287.8; 53/476

(58) Field of Classification Search .................. 422/424; 435/287.8; 53/476
See application file for complete search history.

(56) References Cited

U.S. PATENT DOCUMENTS

| | | | | |
|---|---|---|---|---|
| 6,596,143 | B1 * | 7/2003 | Wang et al. | 204/547 |
| 6,682,702 | B2 | 1/2004 | Barth et al. | |
| 2003/0064507 | A1 * | 4/2003 | Gallagher et al. | 435/287.2 |
| 2003/0235518 | A1 * | 12/2003 | Shea et al. | 422/102 |
| 2005/0282156 | A1 | 12/2005 | Rava et al. | |
| 2007/0070355 | A1 | 3/2007 | Cunningham et al. | |
| 2010/0068101 | A1 * | 3/2010 | Sim et al. | 422/104 |

FOREIGN PATENT DOCUMENTS

| | | | |
|---|---|---|---|
| KR | 100401010 | | 9/2003 |
| KR | 10-0538716 | | 12/2005 |
| WO | 02026377 | A2 | 4/2002 |
| WO | WO2004074835 | * | 9/2004 |
| WO | 2005012561 | A1 | 2/2005 |
| WO | 2006069314 | A1 | 6/2006 |

* cited by examiner

*Primary Examiner* — Lore Jarrett
(74) *Attorney, Agent, or Firm* — Onello & Mello, LLP

(57) ABSTRACT

A package having an improved yield is provided. The package includes a support on which a plurality of biochips are disposed, and a cover bonded to the support and defining a reaction space for each of the plurality of biochips together with the support, the cover including at least one inlet/outlet.

29 Claims, 17 Drawing Sheets

PACKAGES, BIOCHIP KITS AND METHODS OF PACKAGING

CROSS-REFERENCE TO RELATED APPLICATION

This application claims priority to Korean Patent Application No. 10-2007-0070875, filed on Jul. 13, 2007, in the Korean Intellectual Property Office, the disclosure of which is incorporated herein by reference in its entirety.

FIELD OF THE INVENTION

Embodiments of the present invention relate to packages, kits, and packaging methods, for example a wafer-level package containing a reaction space for hybridization, biochip kits, and methods of packaging thereof.

BACKGROUND

In recent years, with the advance of genome projects, the genomic nucleotide sequences of various organisms have been identified. Thus, there has been an increasing interest in biochips, and a variety of biochips are fabricated in the form of kits. Biochip kits are tools that have been widely used in testing various biological samples. The kits provide internal reaction spaces and prevent the biochips from being contaminated or damaged.

In order to fabricate a biochip kit, the biochips are sometimes packaged individually. As an example, widely-used packaging techniques include a method of cutting biochips integrated on a wafer into discrete chips and assembling a package and a biochip one by one. These packaging techniques involve a number of processing steps, which may increase the manufacturing costs and decrease the processing efficiency. In addition, since the surfaces of the biochips formed on a wafer are exposed while undergoing various processing steps, the surfaces of the biochips are prone to damage that can result in a reduction in the reaction efficiency.

SUMMARY OF THE INVENTION

The present invention provides packages having an improved yield, biochip kits having an improved yield, and packaging methods by which a yield can be improved.

According to an aspect of the present invention, there is provided a package including a support on which a plurality of biochips are disposes, and a cover bonded to the support and defining a reaction space for each of the plurality of biochips together with the support, the cover including at least one inlet/outlet.

According to another aspect of the present invention, there is provided a package including a support on which a plurality of biochips are disposed, a spacer bonded to the support and having a plurality of openings corresponding to the plurality of biochips, each of the plurality of openings exposing each of the plurality of biochips, and a cover bonded to the spacer and defining a reaction space for each of the plurality of biochips together with the support and the spacer.

According to still another aspect of the present invention, there is provided a biochip kit including a substrate on which a biochip is disposed, and a cover bonded to the substrate and defining a reaction space over the biochip together with the substrate, the cover including at least one inlet/outlet.

According to a further aspect of the present invention, there is provided a biochip kit including a substrate on which a biochip is disposed, a spacer bonded to the substrate and having an opening corresponding to the biochip, the opening exposing the biochip, and a cover bonded to the spacer and defining a reaction space over the biochip together with the substrate and the spacer, the cover including at least one inlet/outlet.

According to yet another aspect of the present invention, there is provided a packaging method including providing a support on which a plurality of biochips are disposed, and bonding a cover to the support to form a package, the cover including at least one inlet/outlet and defining a reaction space for each of the plurality of biochips together with the support, wherein the cover includes a plurality of cover protrusions, each corresponding to each of the plurality of biochips.

According to a still further aspect of the present invention, there is provided a biochip kit packaging method including providing a support on which a plurality of biochips are disposed, bonding a cover to the support to form a package, the cover including at least one inlet/outlet and defining a reaction space for each of the plurality of biochips together with the support, and cutting the package to separate the plurality of biochips, each biochip having a discrete reaction space.

According to a further aspect of the present invention, there is provided a packaging method including providing a support on which a plurality of biochips are disposed, and bonding a spacer having a plurality of openings corresponding to the plurality of biochips, each of the plurality of openings exposing the plurality of biochips, and bonding a cover to the spacer to form a package, the cover defining a reaction space for each of the plurality of biochips together with the support and the spacer.

According to a further aspect of the present invention, there is provided a biochip kit packaging method including providing a support on which a plurality of biochips are disposed, bonding a spacer having a plurality of openings corresponding to the plurality of biochips, each of the plurality of openings exposing each of the plurality of biochips, bonding a cover to the spacer to form a package, the cover defining a reaction space for each of the plurality of biochips together with the support and the spacer, and cutting the package to separate the plurality of biochips, each having a discrete reaction space.

Other aspects will be described in or be apparent from the following description of the embodiments.

BRIEF DESCRIPTION OF THE DRAWINGS

The above and other features and advantages will become apparent by describing in detail embodiments thereof with reference to the attached drawings in which.

DETAILED DESCRIPTION

Figure 1:
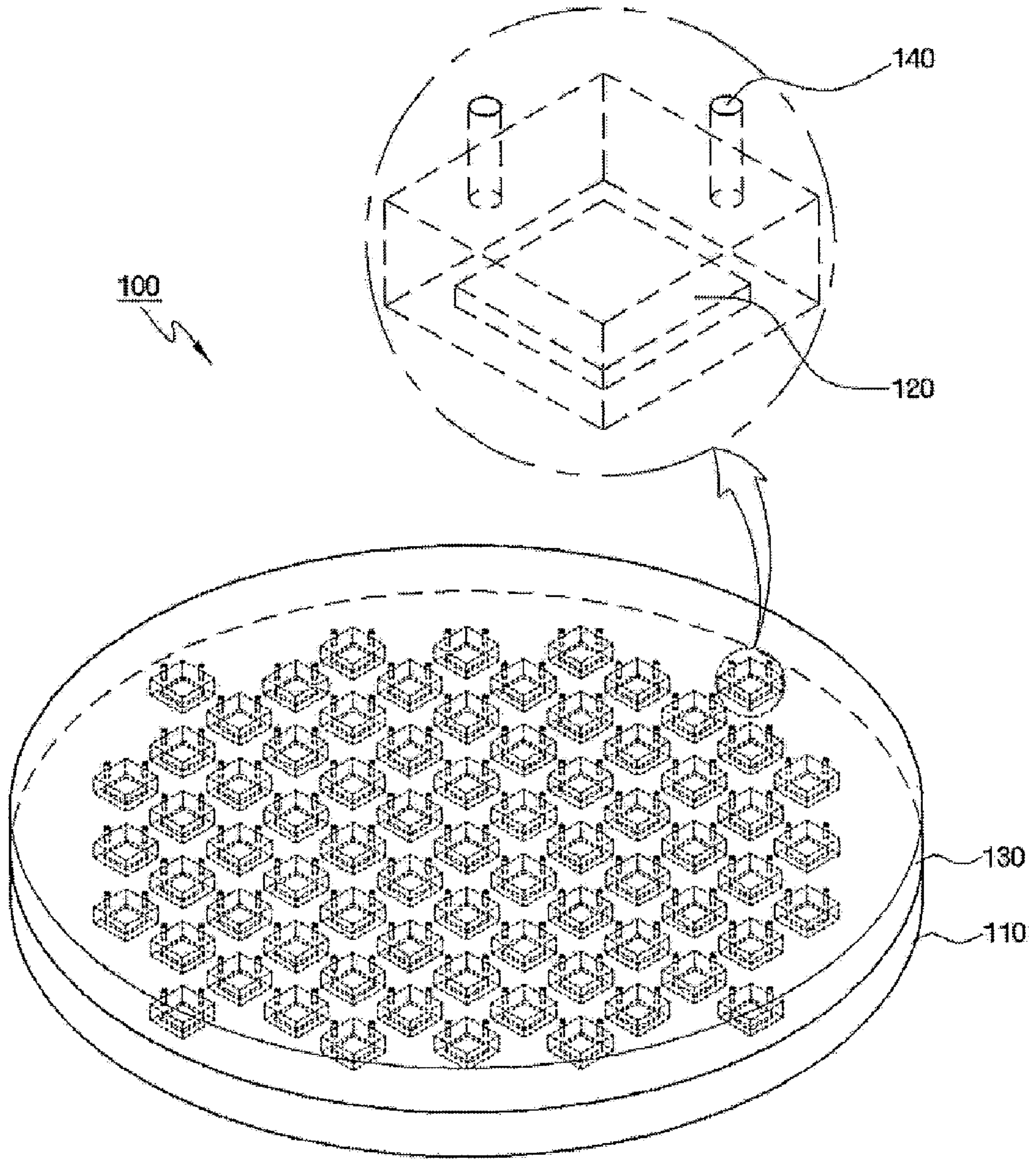
FIG. 1 is a perspective view of a wafer level package according to an embodiment of the present invention.

Other advantages and features of the present invention and methods of accomplishing the same may be understood more readily by reference to the following detailed description of embodiments and the accompanying drawings. The present invention may, however, be embodied in many different forms and should not be construed as being limited to the embodiments set forth herein. Rather, these embodiments are provided so that this disclosure will be thorough and complete and will fully convey the concept of the invention to those skilled in the art. In the drawings, the thickness of layers and regions may be exaggerated or reduced for clarity.

Spatially relative terms, such as “beneath”, “below”, “lower”, “above”, “upper” and the like, may be used herein for ease of description to describe one element or feature’s relationship to another element(s) or feature(s) as illustrated in the figures. It will be understood that the spatially relative terms are intended to encompass different orientations of the device in use or operation in addition to the orientation depicted in the figures. Like reference numerals refer to like elements throughout the specification.

Embodiments will be described with reference to perspective views, cross-sectional views, and/or plan views. The profile of an exemplary view may be modified according to manufacturing techniques and/or allowances. That is, the embodiments of the invention are not intended to limit the scope of the present invention but cover all changes and modifications that can be caused due to a change in manufacturing process.

A wafer level package according to an embodiment of the present invention will first be described with reference to FIGS. 1 through 4.

Figure 2:
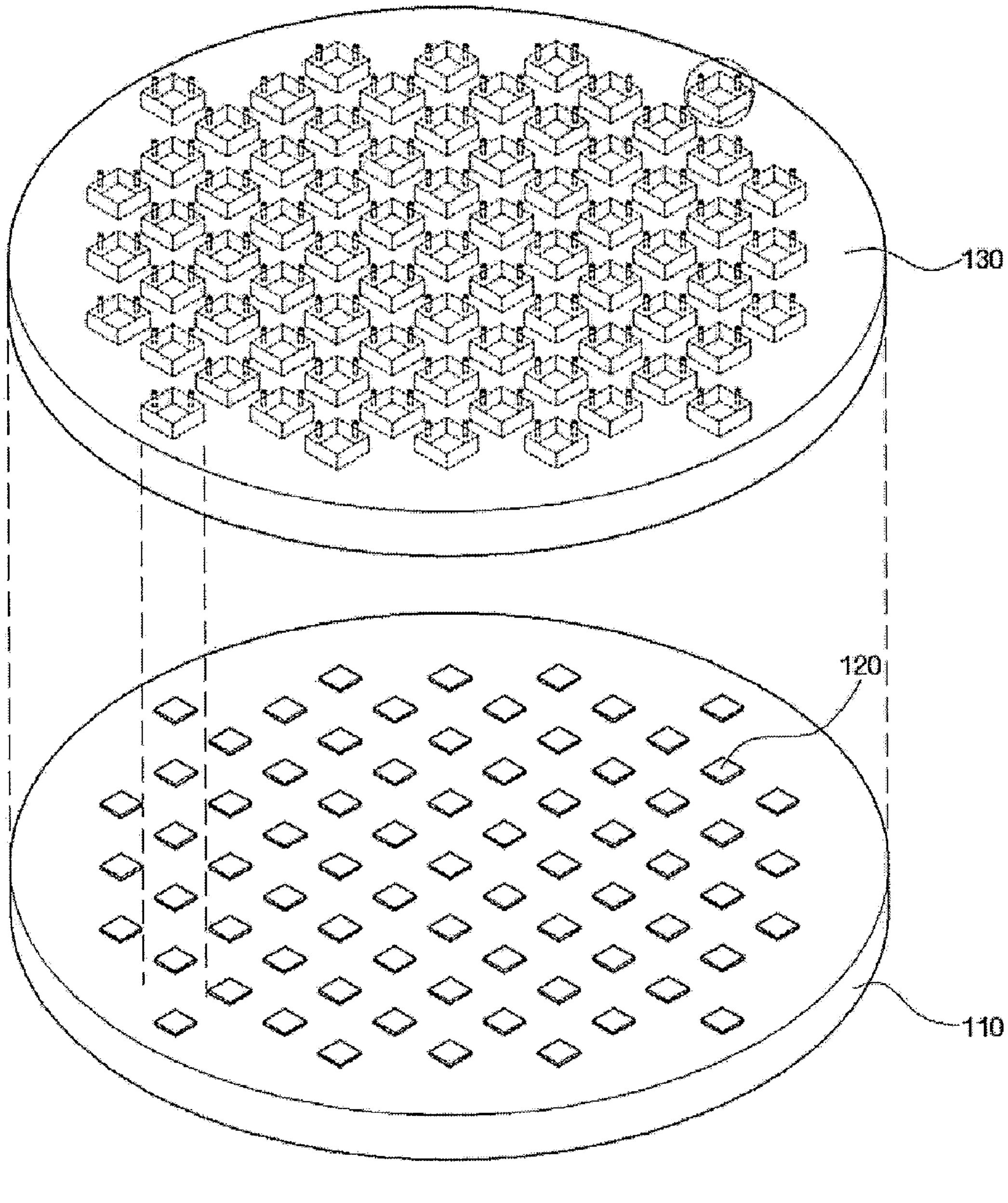
FIG. 2 is an exploded view of the wafer level package shown in FIG. 1.
Figure 3:
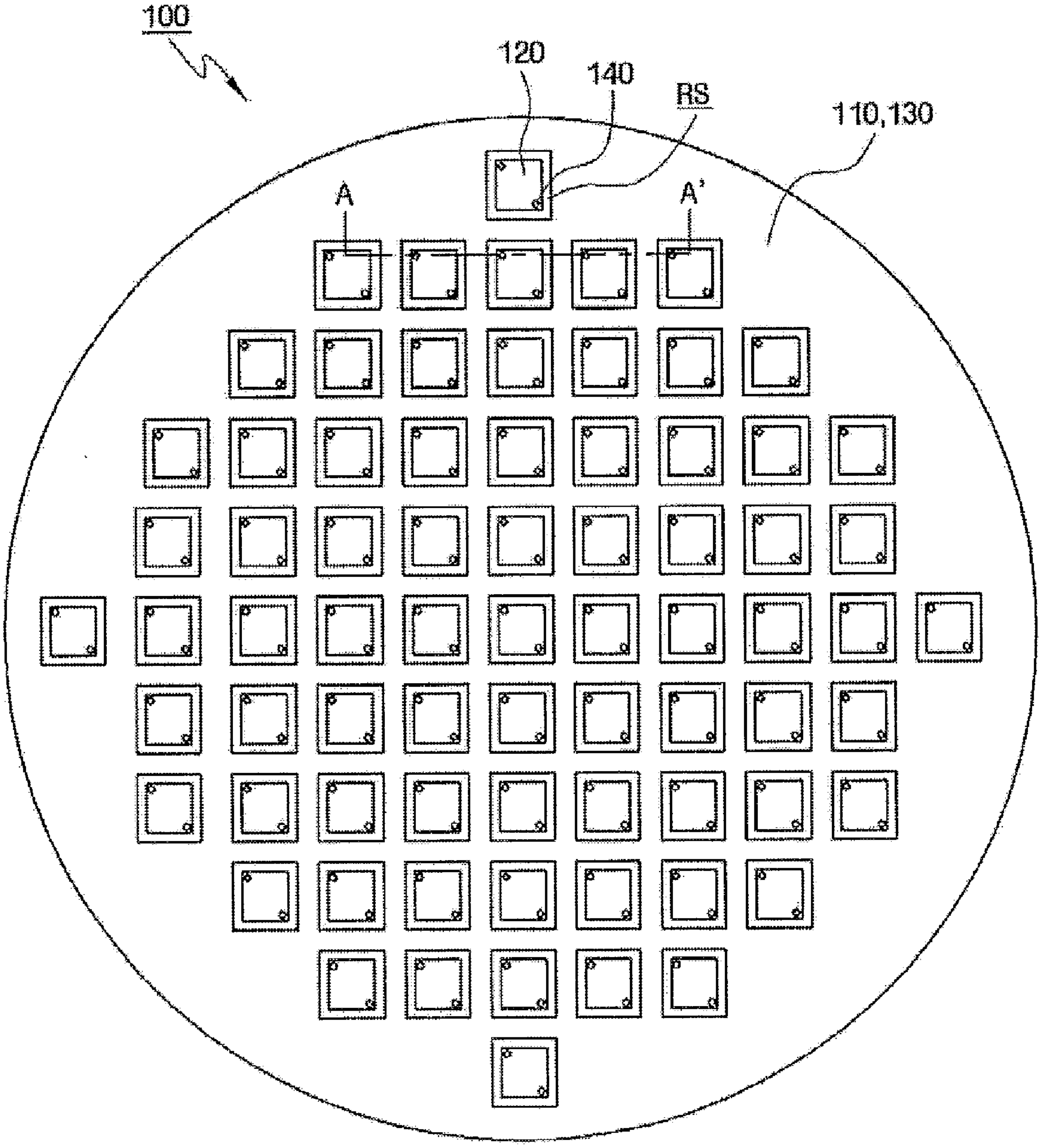
FIG. 3 is a plan view of the wafer level package shown in FIG. 1.
Figure 4:
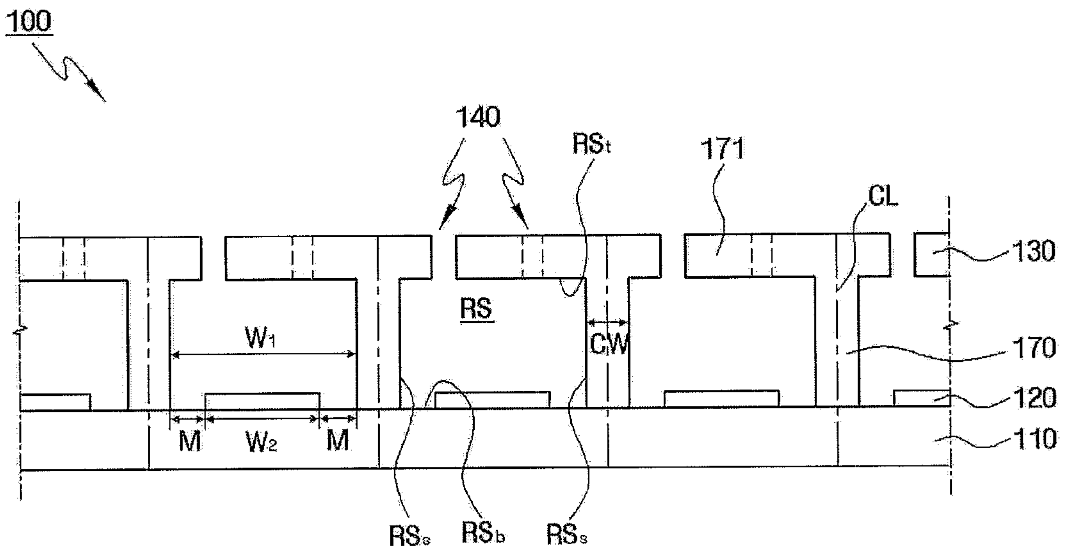
FIG. 4 is a sectional view taken along the line A-A' of FIG. 3.

FIG. 1 is a perspective view of a wafer level package according to an embodiment of the present invention. FIG. 2 is an exploded view of the wafer level package shown in FIG. 1. FIG. 3 is a plan view of the wafer level package shown in FIG. 1. FIG. 4 is a sectional view taken along the line A-A' of FIG. 3.

A wafer level package 100 according to an embodiment of the present invention includes a support wafer 110 on which a plurality of biochips 120 are integrated, and a cover wafer 130 bonded to the support wafer 110 and defining a reaction space RS for each of the plurality of biochips 120 together with the support wafer 110.

The support wafer 110 and the cover wafer 130 may be, for example, an opaque wafer or a transparent wafer. Examples of opaque wafers include a flexible substrate such as a nylon membrane, a nitrocellulose membrane, or a plastic film, or a rigid substrate such as a semiconductor wafer. When a semiconductor substrate is used as the substrate, a semiconductor device fabrication process, various established thin film formation processes, a photolithography process, and others can be used. Examples of transparent wafers include a transparent glass wafer including (e.g., is formed of) soda lime glass, and others. When a fluorescent material detection method using visible light and/or UV light is used in data analysis of biological samples, e.g., a hybridization assay, at least one of the support wafer 110 and the cover wafer 130 may be transparent to the light. For example, the support wafer 110 may be an opaque wafer such as a semiconductor wafer, and the cover wafer 130 may be a transparent glass wafer formed of soda lime glass. When an electrical signal is used in data analysis of a transparent biological sample, both the support wafer 110 and the cover wafer 130 may be opaque. As a result, when an electrical signal method is used, examples of combinations of the support wafer 110 and the cover wafer 130 can be diverse.

A plurality of biochips 120 are integrated on the support wafer 110. Each of the plurality of biochips 120 may be used in, for example, gene expression profiling, genotyping, detection of mutation or polymorphism such as Single-Nucleotide Polymorphism (SNP), assaying of proteins or peptides, potential drug screening, and development and preparation of novel drugs.

The biochip 120 includes active regions (not shown) disposed on the support wafer 110 and a plurality of probes coupled to the active regions. The active regions may be made of a material that is substantially stable against the hydrolysis of the hybridization assay, e.g., upon contact with a pH 6-9 phosphate or a Tris buffer. The active regions may include a silicon oxide layer such as a plasma enhanced-TEOS (PE-TEOS) layer, a high density plasma (HDP) oxide layer, a P—$SiH_4$ oxide layer or a thermal oxide layer; silicate such as hafnium silicate or zirconium silicate; a metal oxynitride layer such as a silicon nitride layer, a silicon oxynitride layer, a hafnium oxynitride layer or a zirconium oxynitride layer; a metal oxide layer such as a titanium oxide layer, a tantalum oxide layer, an aluminum oxide layer, a hafnium oxide layer, a zirconium oxide layer or an indium tin oxide (ITO) layer; polyimide; polyamine; a metal such as gold, silver, copper or palladium; or a polymer such as polystyrene, polyacrylate or polyvinyl.

The plurality of probes may be modified according to test target bio samples. For example, the probes may be oligonucleotide probes. In some embodiments, the coupling between the active regions and the probes may be mediated by linkers interposed therebetween.

The cover wafer 130 includes a plurality of cover wafer protrusions 170 and a plurality of cover wafer bases 171. The cover wafer protrusions 170 are formed such that they protrude from the cover wafer bases 171, and the cover wafer bases 171 and the cover wafer protrusions 170 form recesses corresponding to the biochips 120. The cover wafer protrusions 170 may be formed to correspond to the biochips 120 integrated on the support wafer 110, and shapes of the recesses formed by the cover wafer protrusions 170 may vary without any limitation.

In order to form biochip kits, the cover wafer protrusions 170 are cut along cutting lines CL. However, the cutting process should not damage a reaction space RS. The reaction space RS is defined on each of the biochips 120 by bonding the support wafer 110 and the cover wafer 130. In this regard, the width of each of the cover wafer protrusions 170 and/or the support wafer protrusions 180 (FIG. 5) should be greater than the width damaged by the cutting process. In particular, the width CW of each of the cover wafer protrusions 170 and/or the support wafer protrusions 180 should be greater than the width damaged by the cutting process. For example, when a wafer level package is cut by a sawing process using a 150 μm blade, the maximum width of each of the cover wafer protrusions 170 and/or the support wafer protrusions 180 damaged in one direction may be about 300 μm. In some embodiments, the width CW of each of the cover wafer protrusions 170 and/or the support wafer protrusions 180 may be 750 μm or greater. But to increase the net-die count of biochips per wafer, which is achieved by reducing the width of each protrusion, it is possible to reduce the width of each protrusion to about 300 μm or less.

In addition, at least one inlet/outlet 140 through the cover wafer 130 is formed in each cover wafer bases 171. The inlet/outlet 140 permitting introduction or removal of a fluid such as a biological sample, a cleansing solution, or nitrogen gas, to or from a reaction space RS. The inlet/outlet 140 may be provided in a single body to simultaneously permit introduction or removal of the fluid. Alternatively or additionally, two or more units of the inlet/outlet 140 may be provided, at least one being exclusively for fluid introduction and the others being exclusively for fluid removal. The inlet/outlet 140 may be installed to a fluid supply tube and/or a fluid exhaust tube externally provided. While the illustrated embodiment shows a pair of inlet/outlet 140 alternately formed, the number and position of the inlet/outlet 140 are not limited to the illustrated example.

The plurality of cover wafer protrusions 170 formed on the cover wafer 130 corresponds to the plurality of biochips 120 integrated on the support wafer 110. More specifically, the cover wafer bases 171 are positioned over the biochips 120 and the cover wafer protrusions 170 enclose the biochips 120 to be bonded with support wafer 110. The bonding of the support wafer 110 and the cover wafer 130 may be performed by, for example, anodic bonding, bonding using a sealant, or the like, but not limited thereto.

The reaction space RS defined by bonding the support wafer 110 and the cover wafer 130 is a three-dimensional space defined by a top surface RSt, a bottom surface RSb, and sidewalls RSs connecting the top surface RSt and the bottom surface RSb. In the following example, the reaction space RS has the shape of a quadrilateral pillar, but the shape of the reaction space RS may vary depending on the internal shapes of the cover wafer 130 and the support wafer 110 in other embodiments of the present invention. For example, the reaction space RS may be shaped as a square pillar, a rectangular pillar, a hemispherical pillar, or the like.

The bottom surface RSb of the reaction space RS may be formed by a support wafer 110, the top surface RSt of the reaction space RS may be formed by the cover wafer 130, and the sidewalls RSs of the reaction space RS may be formed by protrusions 170 of the cover wafer 130. In some embodiments, a height of the sidewall RSs may be appropriately set to allow a hybridization reaction between the biochips 120 and the biological sample without causing damages to probes (not shown) formed on the surface of the biochips 120, for example, about 0.1 μm. The height of the sidewall RSs may be a straight line distance between the bottom surface RSb and the top surface RSt of the reaction space RS. The height of the sidewall RSs may be determined by of the amount the cover wafer protrusions 170 extend from the cover wafer bases 171. As a result, the volume of the reaction space RS, for example, to provide a hybridization reaction, may be easily controlled by the height of the cover wafer protrusions 170.

The width W1 of the reaction space RS is the distance between the opposing sidewalls RSs of the reaction space RS. The width W1 of the reaction space RS may be equal to or greater than a width W2 of the biochips 120. In some embodiments, the reaction space RS may enclose edges of the biochips 120 to have a size including a margin M of about 0.5 cm to about 1.5 cm. The hybridization reaction can be facilitated by the margin M.

The reaction space RS may be a substantially closed space. As a result, the biochips 120 can be protected within the reaction space RS from various external contaminants even after various processing steps, such as a binding reaction with a biological sample, and reaction conditions within the reaction space RS can be easily controlled. As used herein, "a substantially closed space" means that the reaction space RS is not only physically perfectly closed but also partially communicatable to and from the environment outside the reaction space RS through holes, like the inlet/outlet 140. Even in embodiments in which the reaction space RS includes the inlet/outlet 140, in order to control the cleanliness or reaction conditions within the reaction space RS, the inlet/outlet 140 may be hermetically sealed by a valve (not shown) or a sealing tape (not shown) while a reaction is being carried out.

Figure 5:
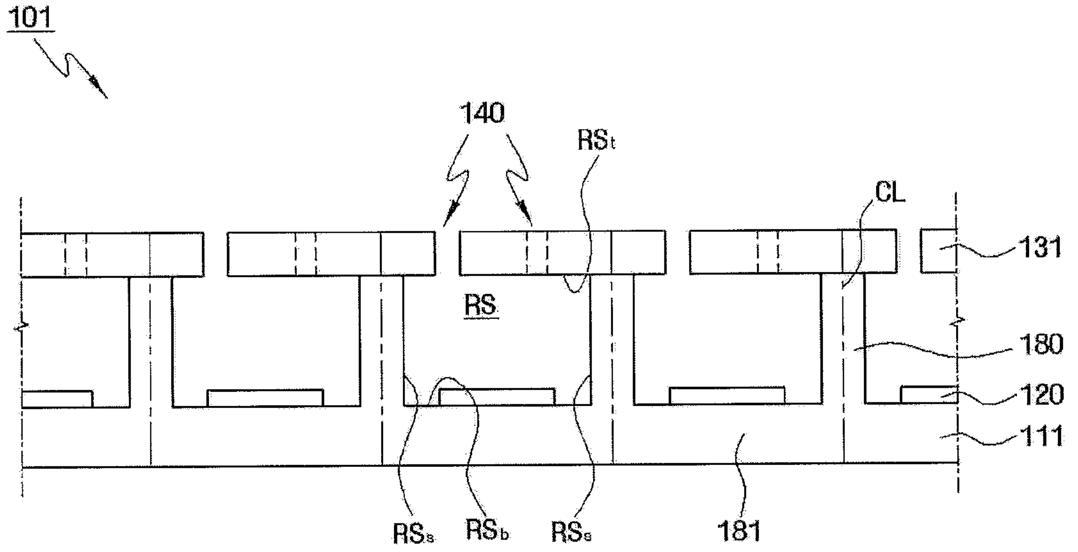
FIGS. 5 and 6 are sectional views of wafer level packages according to another embodiment of the present invention.
Figure 6:
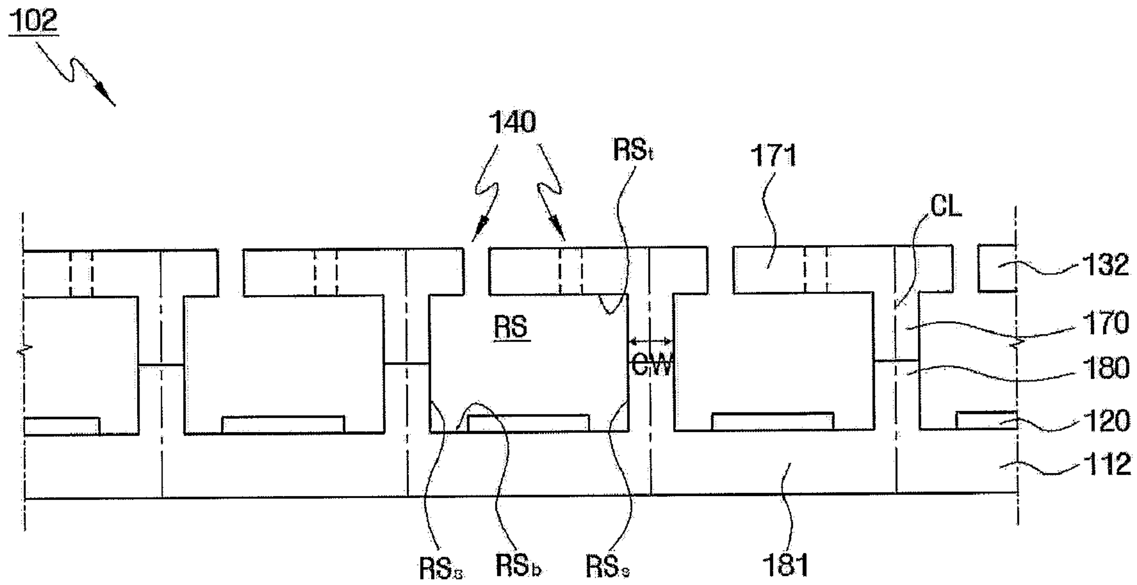

FIGS. 5 and 6 are sectional views of wafer level packages 101, 102 according to another embodiment of the present invention. The wafer level packages 101 and 102 are substantially the same as the wafer level package according to the previous embodiment of the present invention (see 100 of FIG. 4), except for the construction of the sidewall RSs of the reaction space RS. In the wafer level packages 100, 101 and 102 according to some embodiments of the present invention, the bottom surface RSb of the reaction space RS may be formed by the support wafer 110, 111, and 112 alone, and the top surface RSt of the reaction space RS may be formed by the cover wafer 130, 131, and 132 alone. In addition, the sidewalls RSs of the reaction space RS may be formed by the cover wafer 130 or support wafer 111 alone or a combination of the support wafer 112 and the cover wafer 132. When the sidewalls RSs of the reaction space RS are formed by the cover wafer 130 alone, as stated above, cover wafer protrusions (see 170 FIG. 2) are provided by the cover wafer 130. In the case where support wafer protrusions 180 are provided by the support wafer 111, as shown in FIG. 5, the sidewalls RSs of the reaction space RS may be formed by the support wafer 111 alone. As shown in FIG. 6, in a case where the protrusions 170 and 180 are provided by both the cover wafer 132 and the support wafer 112, and the cover wafer 132 and the support wafer 112 are bonded by their protrusions, the sidewalls RSs of the reaction space RS may be formed by the support wafer 112.

The wafer level packages described herein can be used in manufacturing biochip kits. A plurality of biochip kits can be more easily obtained by spatially isolating a plurality of reaction spaces formed in the wafer level packages. As a result, the processing efficiency can be improved and the manufacturing costs can be reduced.

Figure 7:
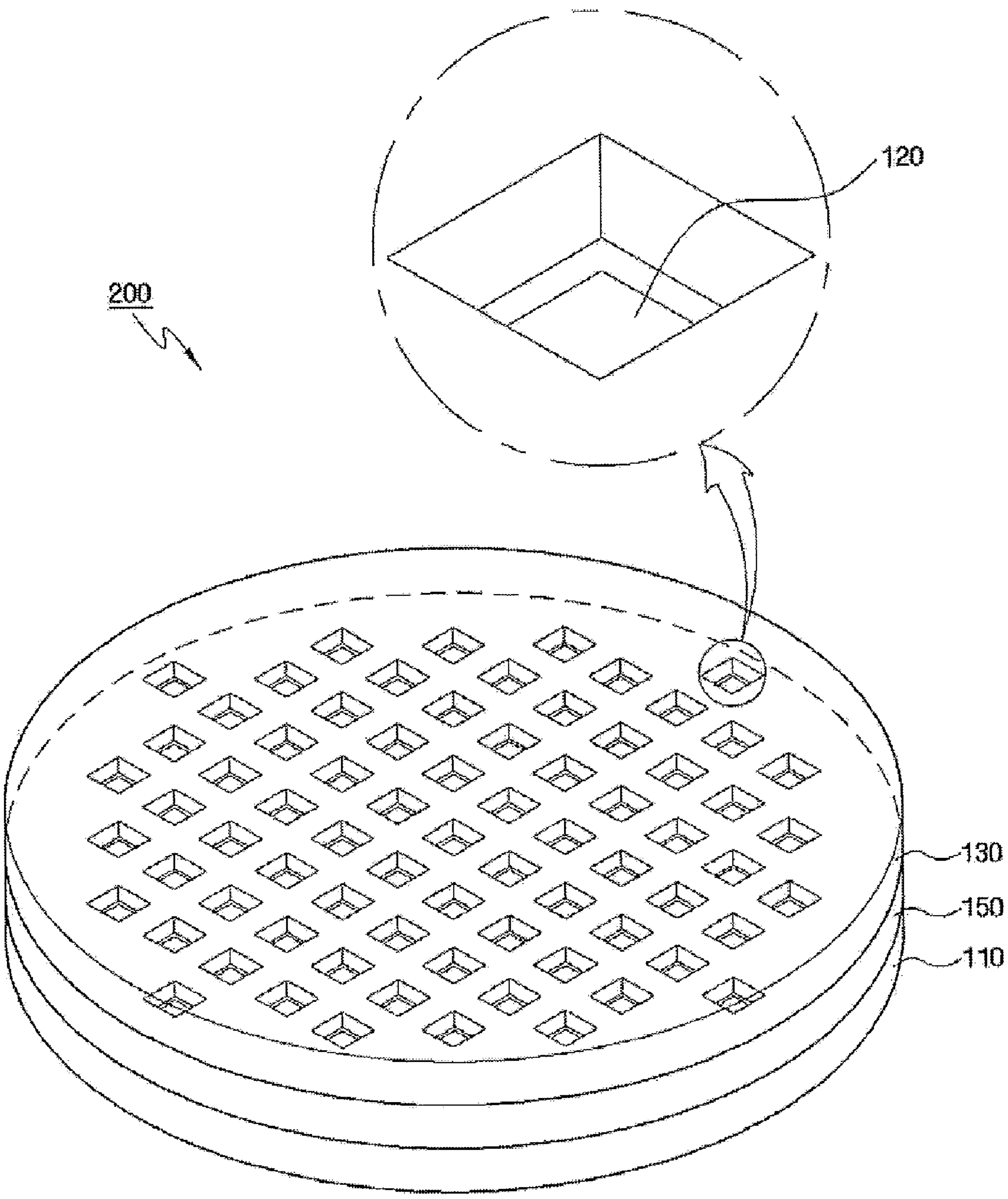
FIG. 7 is a perspective view of a wafer level package according to still another embodiment of the present invention.
Figure 8:
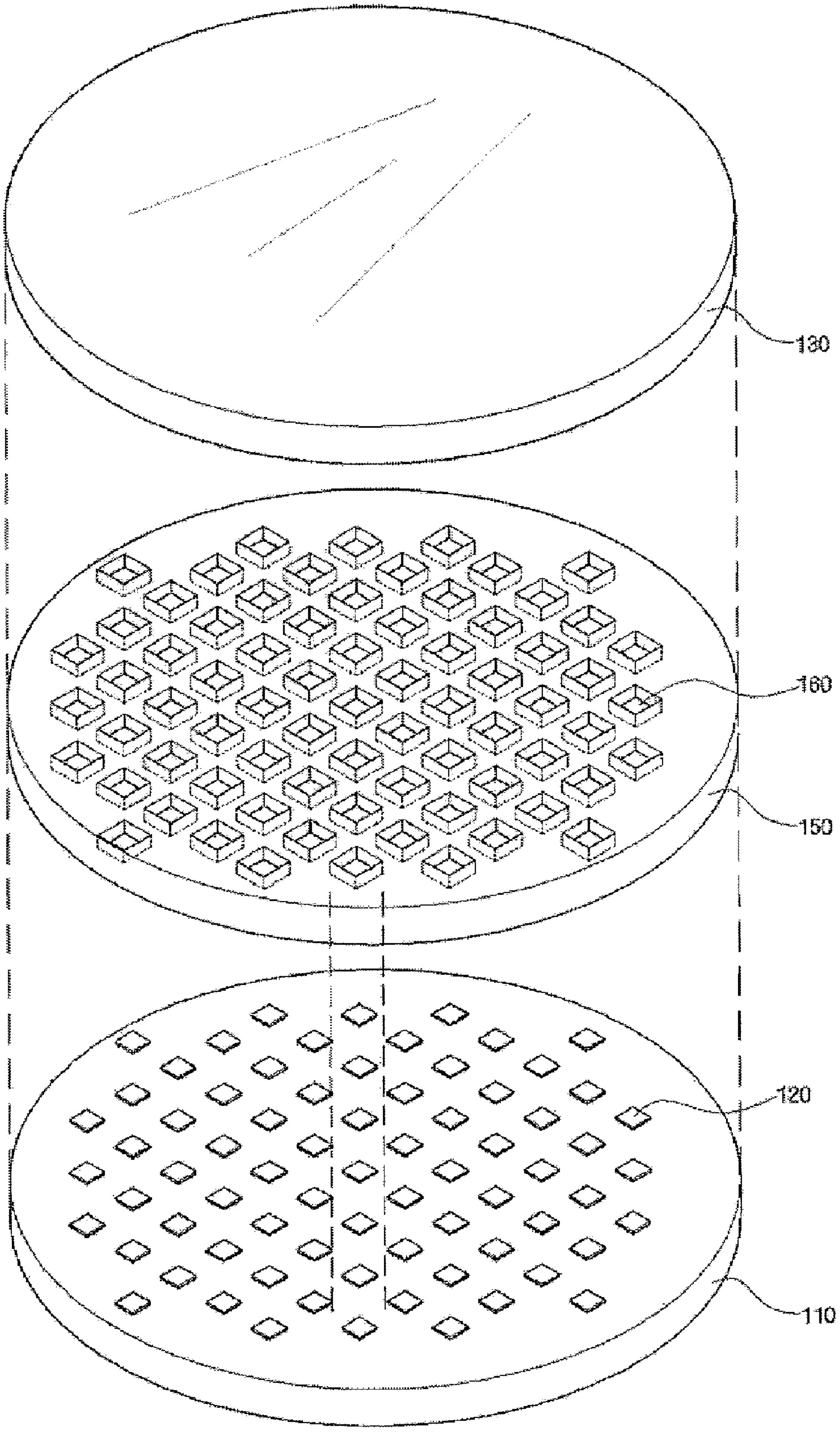
FIG. 8 is an exploded view of a wafer level package according to still another embodiment of the present invention.
Figure 9:
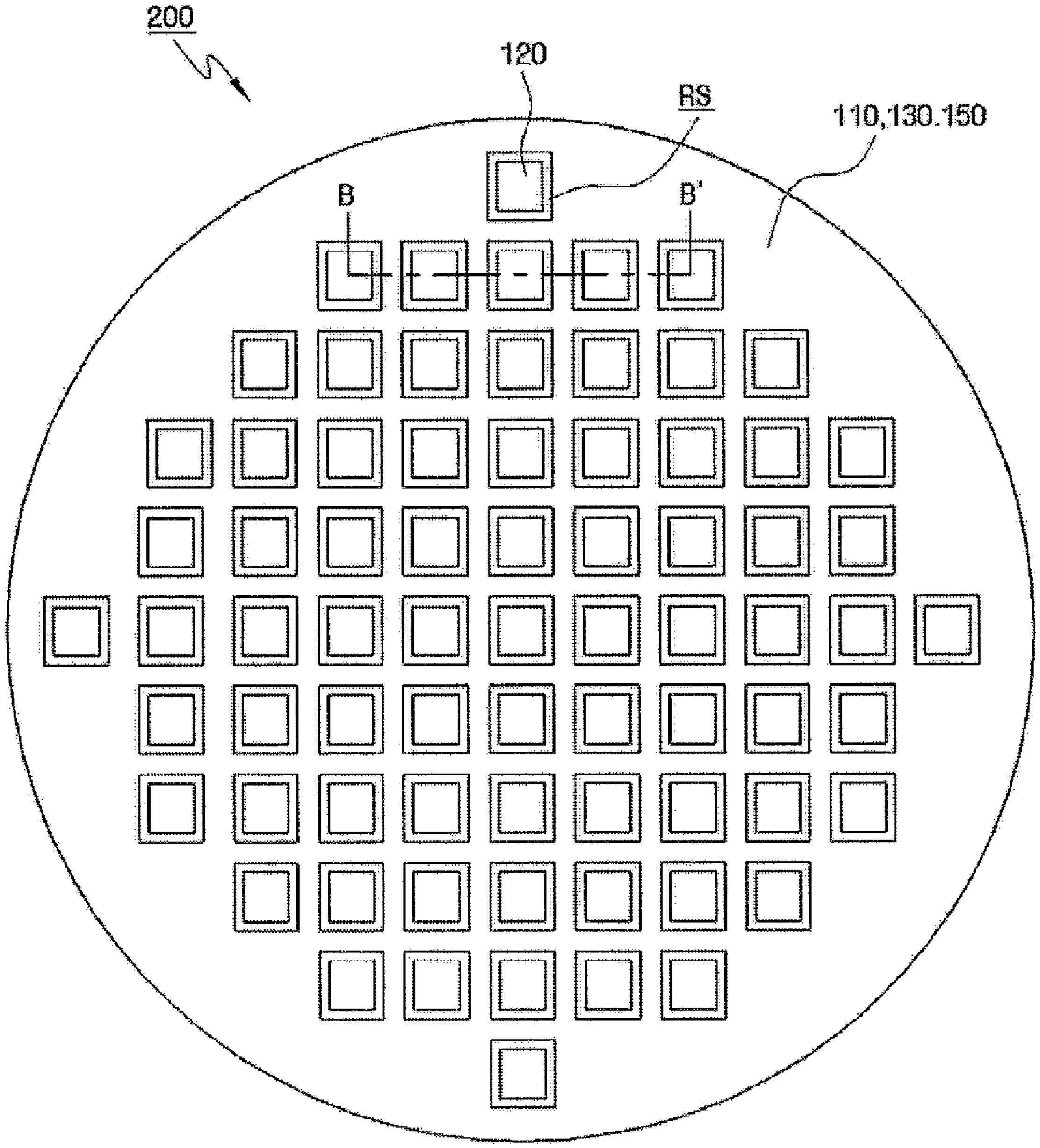
FIG. 9 is a plan view of a wafer level package according to still another embodiment of the present invention.
Figure 10:
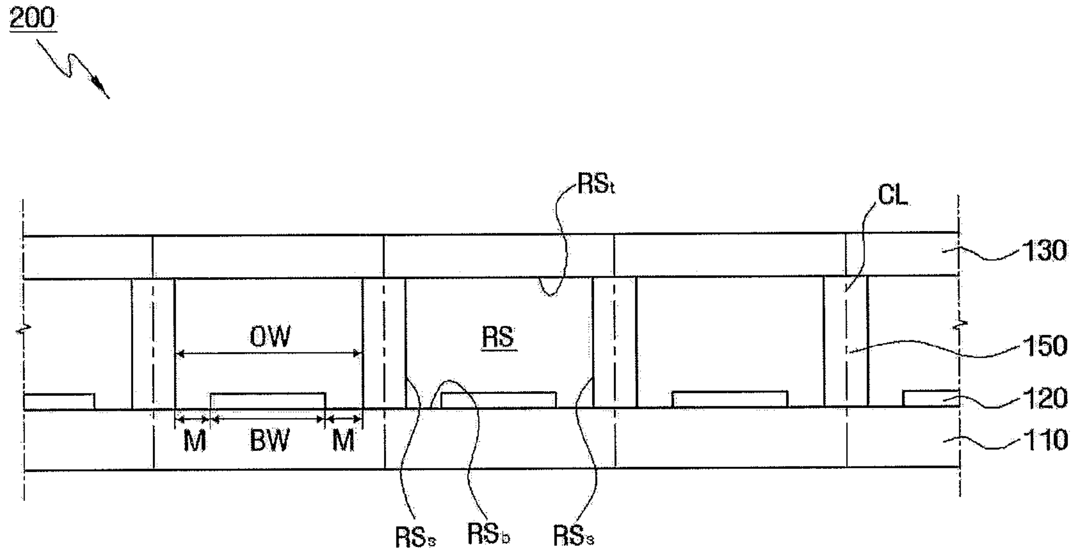
FIG. 10 is a sectional view taken along the line B-B' of FIG. 9.

A wafer level package according to still another embodiment of the present invention will now be described with reference to FIGS. 7 through 10. FIG. 7 is a perspective view of a wafer level package according to still another embodiment of the present invention, illustrating a state in which a support wafer, a spacer wafer and a cover wafer are bonded together. FIG. 8 is an exploded view of the wafer level package shown in FIG. 7, illustrating a state in which a support wafer, a spacer wafer and a cover wafer are disconnected from one another. FIG. 9 is a plan view of the wafer level package shown in FIG. 7. FIG. 10 is a sectional view taken along the line B-B' of FIG. 9.

Referring to FIGS. 7-10, the wafer level package 200 according to still another embodiment of the present invention includes a support wafer 110 on which a plurality of biochips 120 are integrated, a spacer wafer 150 bonded to the support wafer 110 and having a plurality of openings 160 corresponding to the plurality of biochips 120, each of the plurality of openings 160 exposing a biochip 120, and a cover wafer 130 bonded to the spacer wafer 150 and defining a reaction space RS for each of the plurality of biochips 120 together with the support wafer 110 and the spacer wafer 150. The wafer level package 200 is substantially the same as the wafer level packages 100, 101, and 102 except that the spacer wafer 150 is further provided on the support wafer 110. The support wafer 110 and biochips 120 integrated on the support wafer 110 are the same as those described above.

The spacer wafer 150 may be an opaque wafer or a transparent wafer, like the support wafer 110 and the cover wafer 130. Examples of the spacer wafer 150 are the same as described above. In addition, the spacer wafer 150 may be, for example, made of a self-sealing material, such as rubber, silicone or urethane. When the spacer wafer 150 is made of rubber, silicone or urethane, various fluids can be introduced and removed through the spacer wafer 150 using a pipette, a syringe, or the like. That is, the spacer wafer 150 may serve as the inlet/outlet. After a predetermined fluid is introduced or removed through the spacer wafer 150, the pipette or the syringe is removed from the spacer wafer 150, the hole generated due to the use of the pipette or the syringe may be reduced or resealed. Therefore, it is possible to form a resealable and self-sealing reaction space RS without an additional sealing process. It is not necessary to form a separate inlet/outlet in the cover wafer 130. The wafer level package fabrication process can be greatly simplified by omitting formation of the separate inlet/outlet on the wafer level package, the processing efficiency can be improved, and the manufacturing costs can be reduced.

As shown, the spacer wafer 150 includes a plurality of openings 160 and is bonded to the support wafer 110. Each of the plurality of openings 160 extends through the spacer wafer 150. More specifically, the plurality of openings 160 are formed to be spaced apart from each other and corresponds to the biochips 120 integrated on the support wafer 110. As described above, a margin M may be provided to enclose edges of the biochips 120, e.g., in order to facilitate a hybridization reaction. A width OW of the openings 160 may be equal to or greater than a width BW of the biochips 120 in consideration of the margin M.

The spacer wafer 150 is bonded to the support wafer 110 such that the plurality of openings 160 corresponds to the plurality of biochips 120. The biochips 120 are exposed to the environment through the plurality of openings 160 of the spacer wafer 150 bonded to the support wafer 110. However, since the cover wafer 130 is further formed on the spacer wafer 150, the biochips 120 are not directly exposed to the environment. Even if the biochips 120 are exposed when the cover wafer 130 is not formed, after forming the spacer wafer 150, the biochips 120 are sealed and are not exposed to the external environment until a biochip-using step (e.g., until the biochip is reacted with a reaction solution.). The bonding between the support wafer 110 and the spacer wafer 150 or between the spacer wafer 150 and the cover wafer 130 may be performed by, for example, anodic bonding, bonding using a sealant, or the like, but not limited thereto.

As shown in FIG. 10, the plurality of biochips 120 integrated on the support wafer 110 are spatially isolated from one another by the spacer wafer 150, so that a discrete reaction space RS is formed for each of the biochips 120. In each reaction space RS, the spatially isolated biochips 120 may be subjected to hybridization reactions with a variety of kinds of biological samples.

The reaction space RS is defined for each of the biochips 120 by bonding the support wafer 110 and the cover wafer 130 with the spacer wafer 150. A top surface RSt and a bottom surface RSb forming the reaction space RS are the same as described above.

Figure 11:
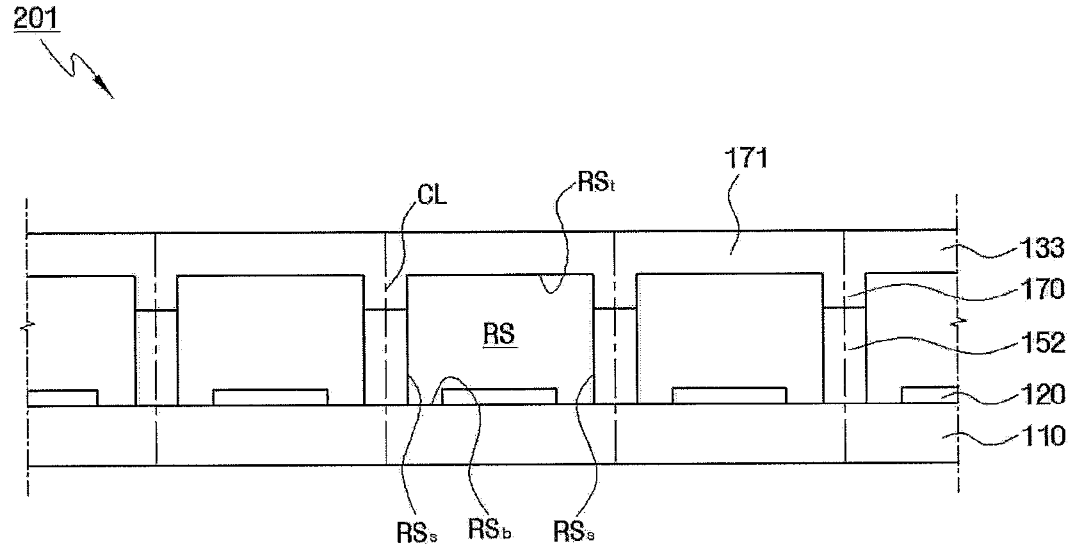
FIGS. 11 through 14 are sectional views of wafer level packages according to still another embodiment of the present invention.
Figure 12:
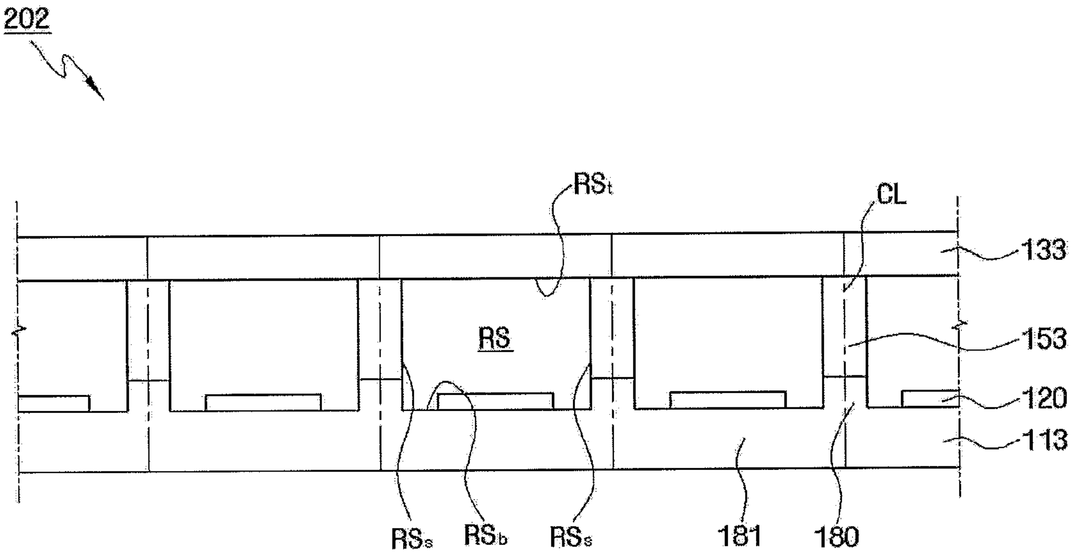
Figure 13:
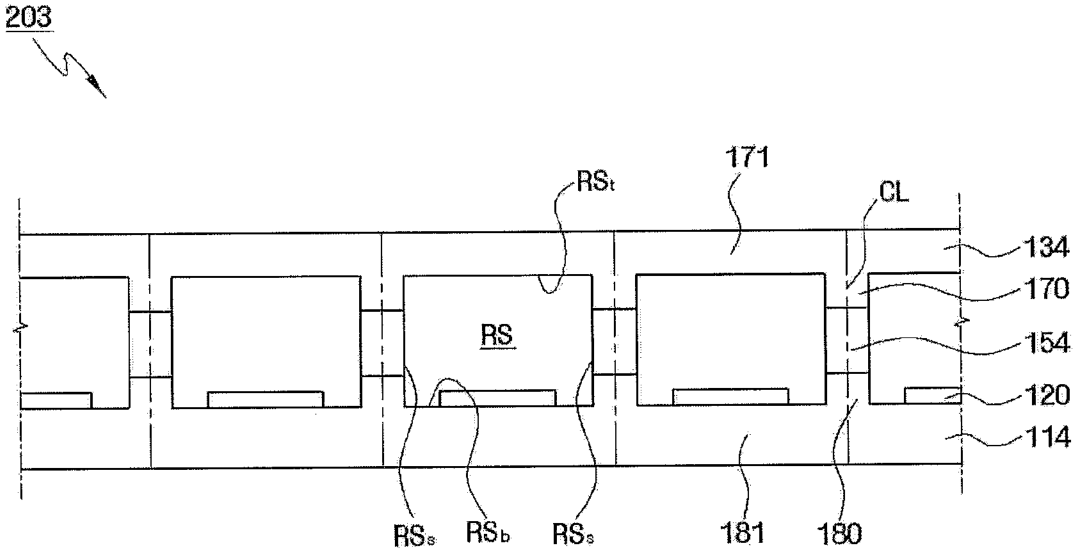

FIGS. 11 through 13 are sectional views of wafer level packages 201, 202, and 203 according to still another embodiment of the present invention. The wafer level packages 201, 202, and 203 are substantially the same as the wafer level package 200 illustrated in FIGS. 7 through 10, except for sidewalls RSs of the reaction space RS, which will now be described in more detail.

The sidewalls RSs of the reaction space RS may be formed by the spacer wafer 150 alone (see FIG. 10), or a combination of the support wafer 110 and/or the cover wafer 130 with the spacer wafer 150. As shown in FIG. 11, a reaction space RS may be formed by bonding a spacer wafer 152 to a cover wafer 133 including a plurality of cover wafer protrusions 170 such that the cover wafer protrusions 170 are aligned with openings (see 160 of FIG. 8) of the spacer wafer 152. That is, the sidewalls RSs of the reaction space RS may be formed by the cover wafer 133 and the spacer wafer 152. The height of the reaction space RS may be determined by the length of the cover wafer protrusions 170 and the thickness of the spacer wafer 152. The volume of the reaction space RS may be easily controlled by the height of the cover wafer protrusions 170 and the thickness of the spacer wafer 152. The sidewalls RSs of the reaction space RS may also be formed by the support wafer 113 and the spacer wafer 153 by forming a plurality of support wafer protrusions on the support wafer 113 (see FIG. 12). In addition, the sidewalls RSs of the reaction space RS may be formed by forming the plurality of protrusions on both the support wafer 114 and the cover wafer 134 and bonding the same to the spacer wafer 154 so as to face the top surface and bottom surface of the spacer wafer 154 (see FIG. 13).

Figure 14:
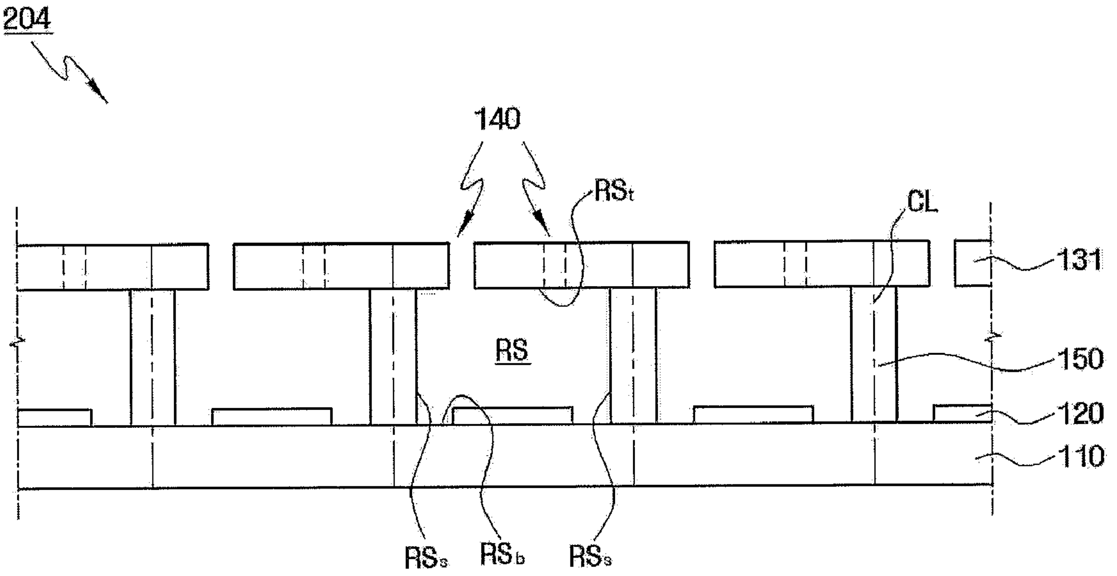

FIG. 14 is a sectional view of a wafer level package 204 according to still another embodiment of the present invention. The wafer level package 204 is different from the wafer level packages 200, 201, 202, and 203 according to the previous embodiments in that at least one inlet/outlet 140 is provided in the cover wafer 131. The inlet/outlet 140 is substantially the same as described above, and a detailed explanation thereof will not be given. FIG. 14 illustrates a modification of the wafer level package (200 of FIG. 10) having the sidewalls RSs of the reaction space formed by the spacer wafer 150 alone. The wafer level package 204 shown in FIG. 14 includes a cover wafer 131 having the inlet/outlet 140. In some embodiments, the wafer level packages 201, 202, and 203 may comprise cover wafers 133, 130, and 134 having at least one inlet/outlet, respectively.

In the wafer level packages according to some embodiments of the present invention, it is not necessary to form a separate inlet/outlet, depending on the material of the spacer wafer 150. As a result, the processing efficiency can be improved and the manufacturing costs can be reduced. In addition, a spatial margin of the reaction space RS is provided by the spacer wafer 150, thereby facilitating hybridization reactions using the biochips 120. Further, the wafer level package is divided by spatially discrete reaction spaces, thereby easily obtaining a plurality of biochip kits.

Figure 15:
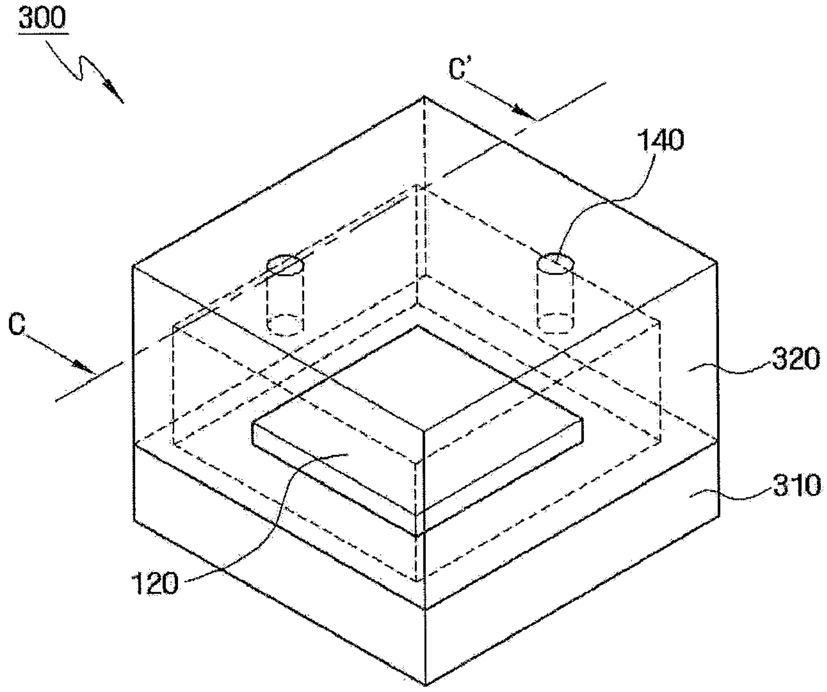
FIG. 15 is a perspective view of a biochip kit according to an embodiment of the present invention.

Biochip kits according to some embodiments of the present invention will be described with reference to FIGS. 15 through 25. FIG. 15 is a perspective view of a biochip kit according to an embodiment of the present invention, FIG. 16 is a sectional view taken along the line C-C' of FIG. 15, and FIGS. 17 and 18 are sectional views of biochip kits according to some embodiments of the present invention.

The biochip kits 300, 301, and 302 according to some embodiments of the present invention are fabricated by dividing the wafer level packages 100, 101, and 102 according to some embodiments of the present invention into separate reaction spaces RS. The biochip kits are formed by separating the cover wafer protrusions 170 and/or support wafer protrusions 180.

Figure 16:
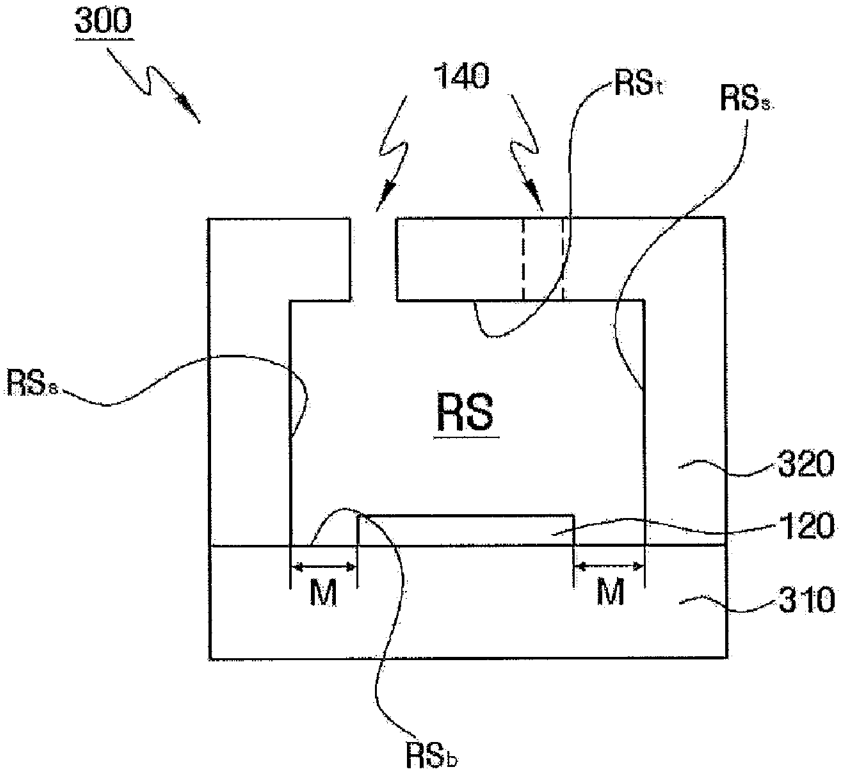
FIG. 16 is a sectional view taken along the line C-C' of FIG. 15.
Figure 17:
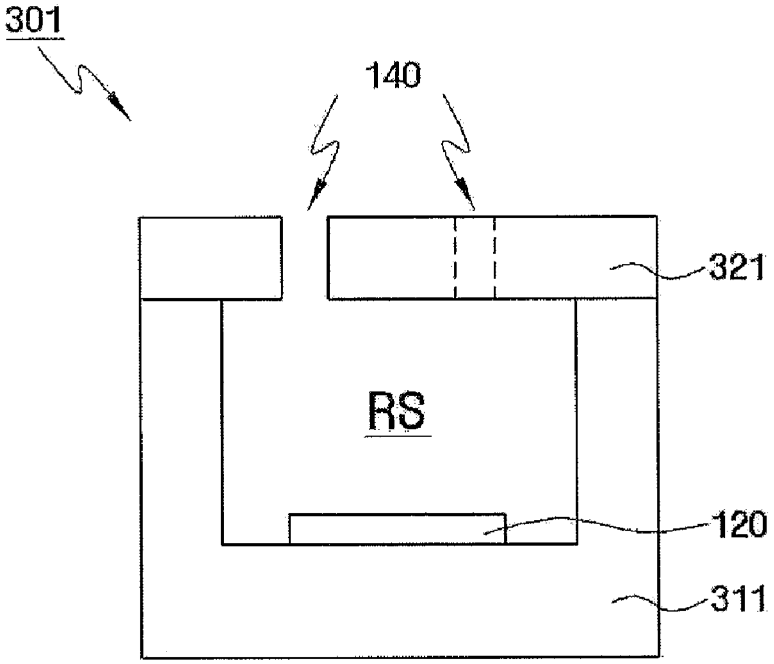
FIGS. 17 and 18 are sectional views of biochip kits according to some embodiments of the present invention.
Figure 18:
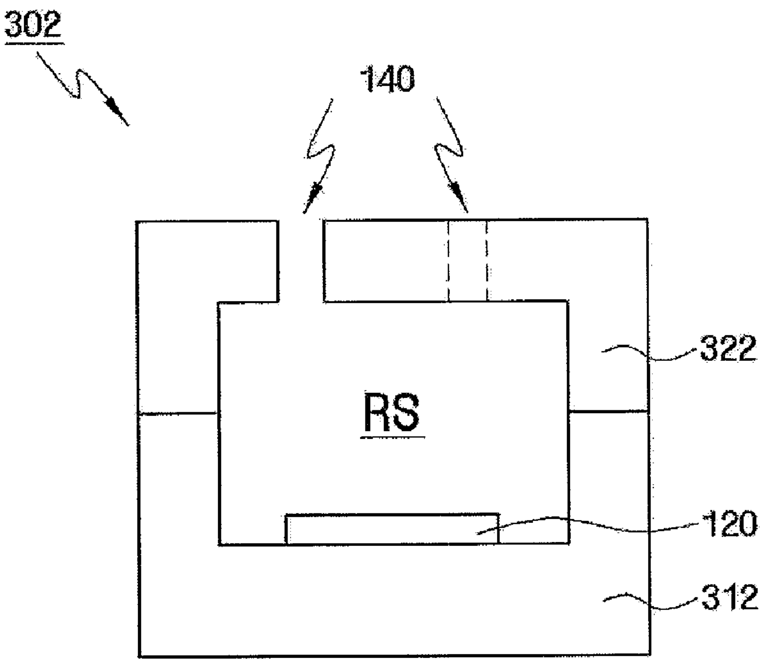
Figure 19:
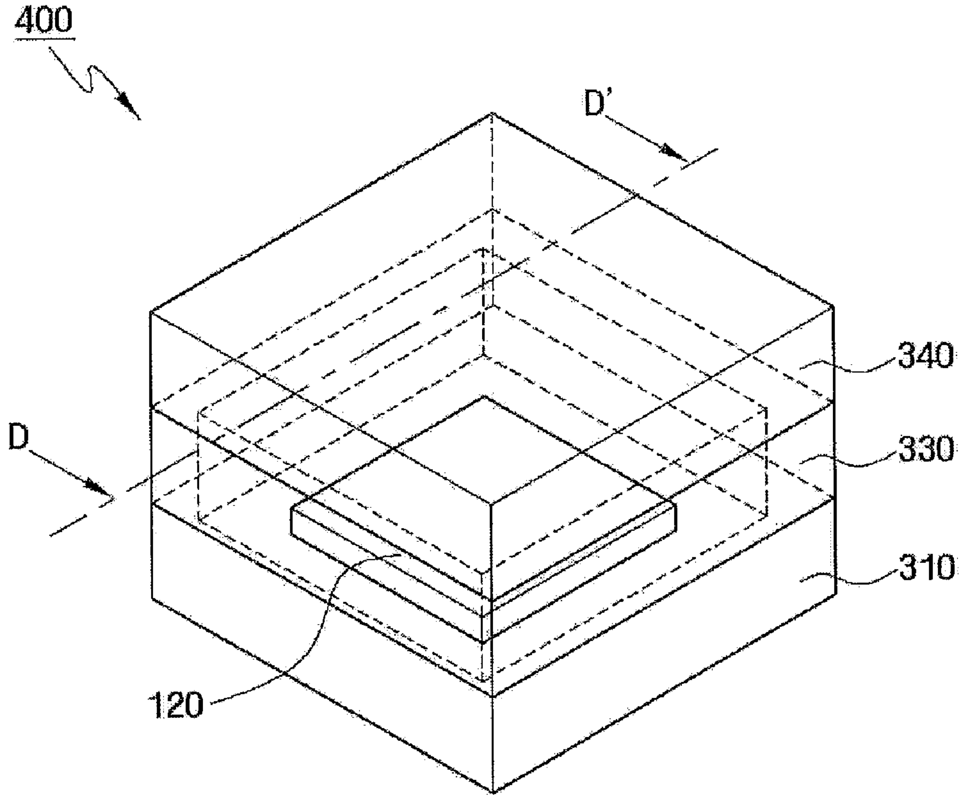
FIG. 19 is a perspective view of a biochip kit according to another embodiment of the present invention.
Figure 20:
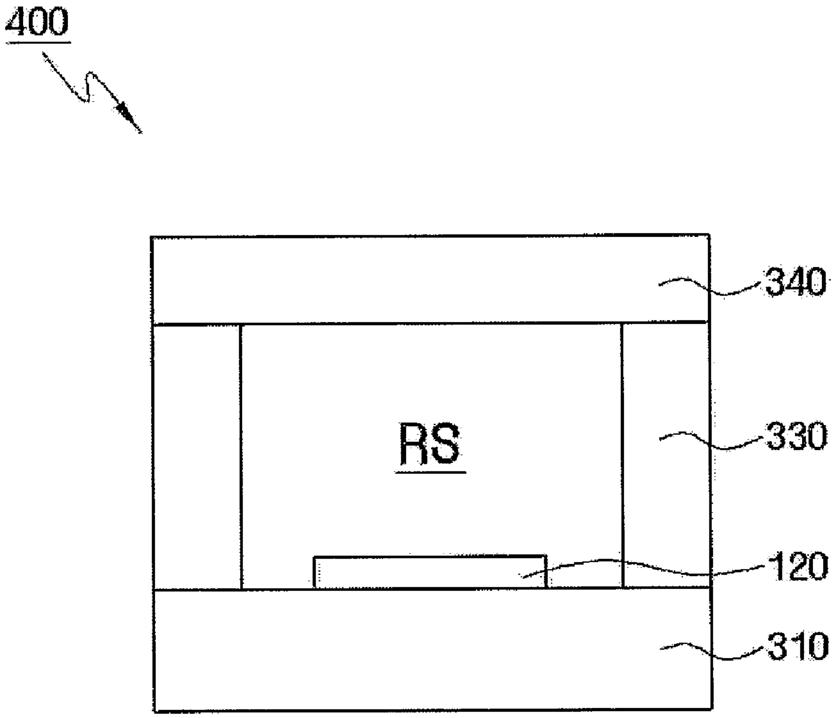
FIG. 20 is a sectional view taken along the line D-D' of FIG. 19.

For example, the biochip kits 300, 301, and 302 shown in FIGS. 16 through 18 are obtained by cutting the wafer level packages 100, 101, and 102 shown in FIGS. 4 through 6 along the cutting line CL. Biochip kits 400, 401, 402, 403, and 404 according to some other embodiments of the present invention, as shown in FIGS. 20 and 22 through 25, are fabricated by cutting the wafer level packages 200, 201, 202, 203, and 204 according to some other embodiments of the present invention, as shown in FIGS. 10 through 14, along the cutting line CL.

As described above, the biochip kits according to some embodiments of the present invention are fabricated by dividing the wafer level packages according to some embodiments of the present invention into separate reaction spaces RS, and since functional components thereof are substantially the same as described above, a detailed explanation will not be given.

A substrate 310 biochip 120 is formed on a substrate 310. An area of the bottom surface RSb of a reaction space RS may be greater than that of the biochip 120. The biochip 120 may be constructed so as not contact sidewalls RSs of the reaction space RS. For example, the biochip 120 may be centrally positioned on the bottom surface RSb of the reaction space RS. The reaction space RS may enclose edges of the biochip 120 to have a margin M of about 0.5 cm to about 1.5 cm. The margin M provided around the biochip 120 can prevent a hybridization reaction between the biochip 120 and a biological sample.

Figure 21:
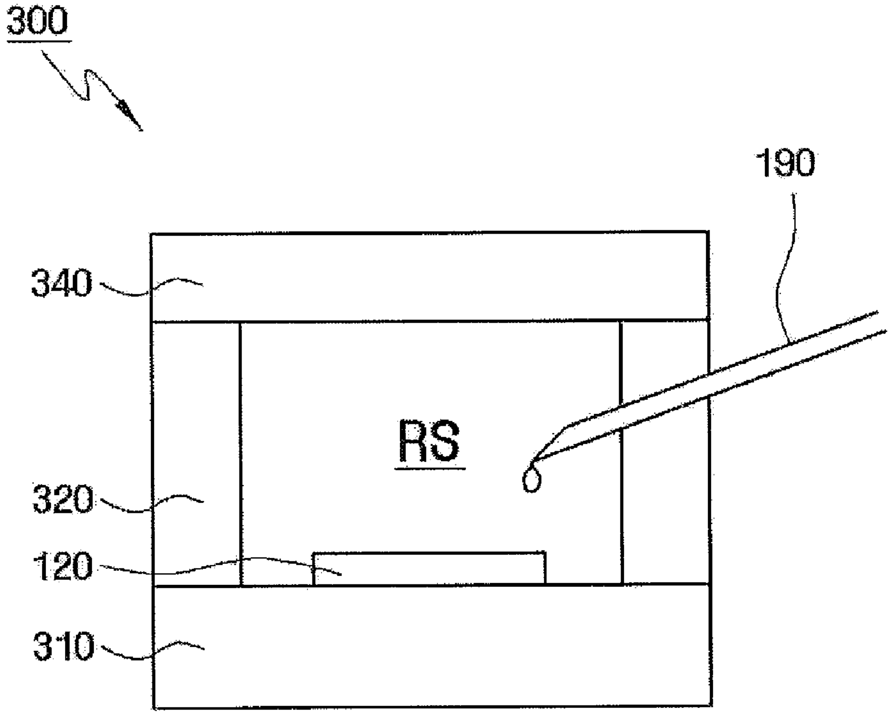
FIG. 21 is a sectional view of a biochip kit, illustrating a state in which the biochip kit is used.
Figure 22:
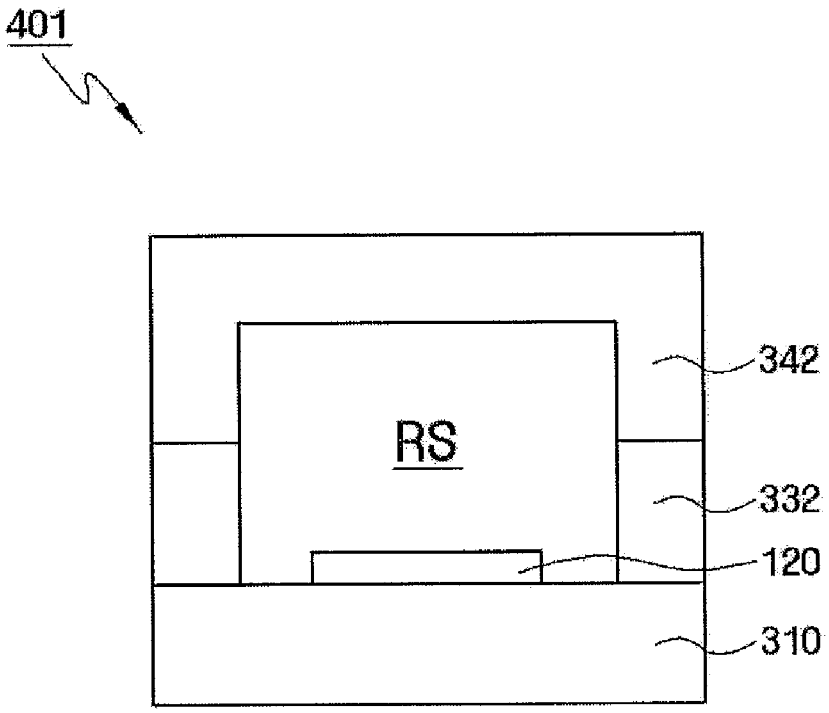
FIGS. 22 through 25 are sectional views of biochip kits according to some embodiments of the present invention.
Figure 23:
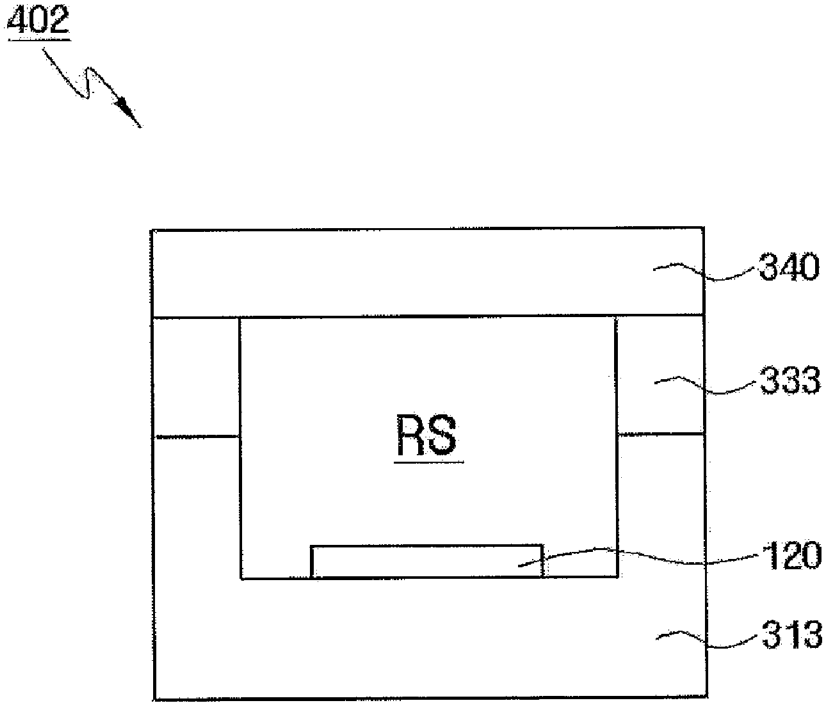
Figure 24:
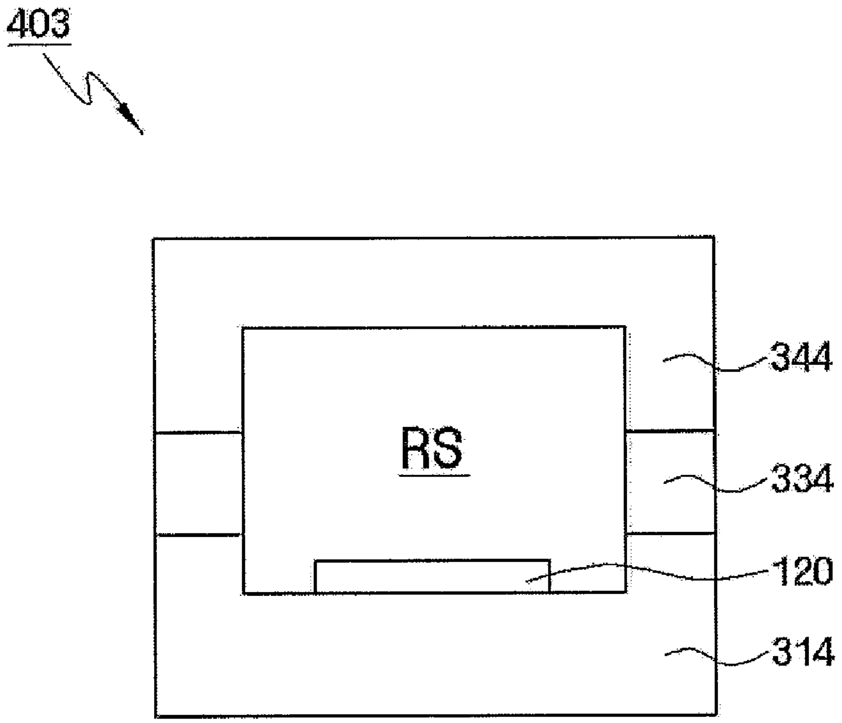
Figure 25:
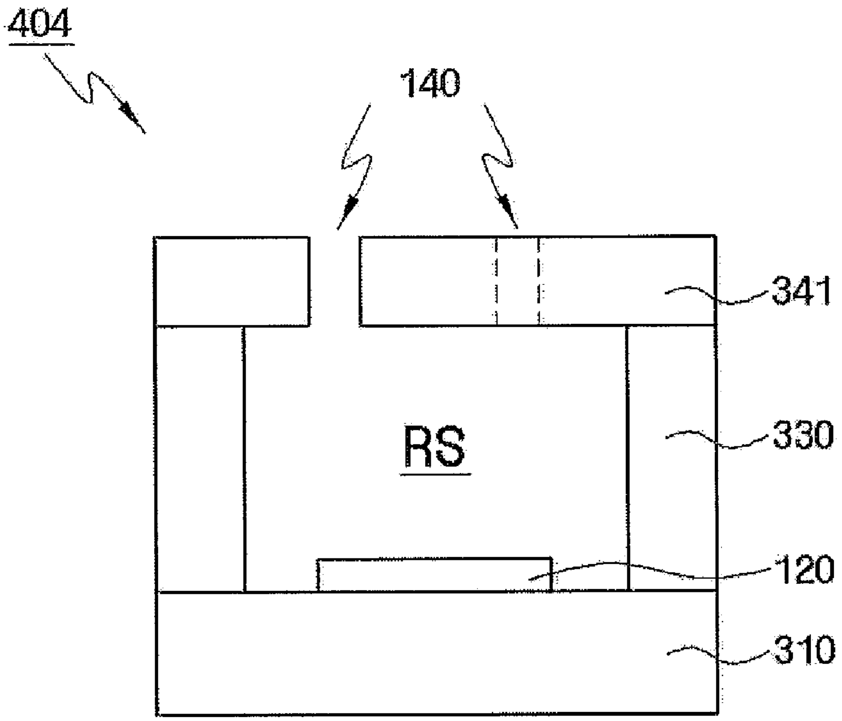

FIG. 21 is a sectional view illustrating an exemplary method of supplying a fluid through a spacer 330. Referring to FIG. 21, when the spacer 330 is made of a self-sealing material (such as silicone or urethane), various fluids can be introduced and removed through the spacer wafer 330 using a fine tube 190 such as a pipette or a syringe. For example, after a predetermined fluid is introduced or removed through the spacer 330 using the fine tube 190, the fine tube 190 is removed from the spacer 330 and a path serving as an inlet/outlet may be resealed, producing a resealed reaction space RS. That is, the spacer 330 may serve as the inlet/outlet. If the spacer 330 serves as the inlet/outlet, it may not be necessary to form a separate inlet/outlet 140 in the cover 320. The wafer level package fabrication process can be greatly simplified by omitting formation of the separate inlet/outlet 140 in the cover 320, the processing efficiency can be improved, and the manufacturing costs can be reduced.

Figure 26:
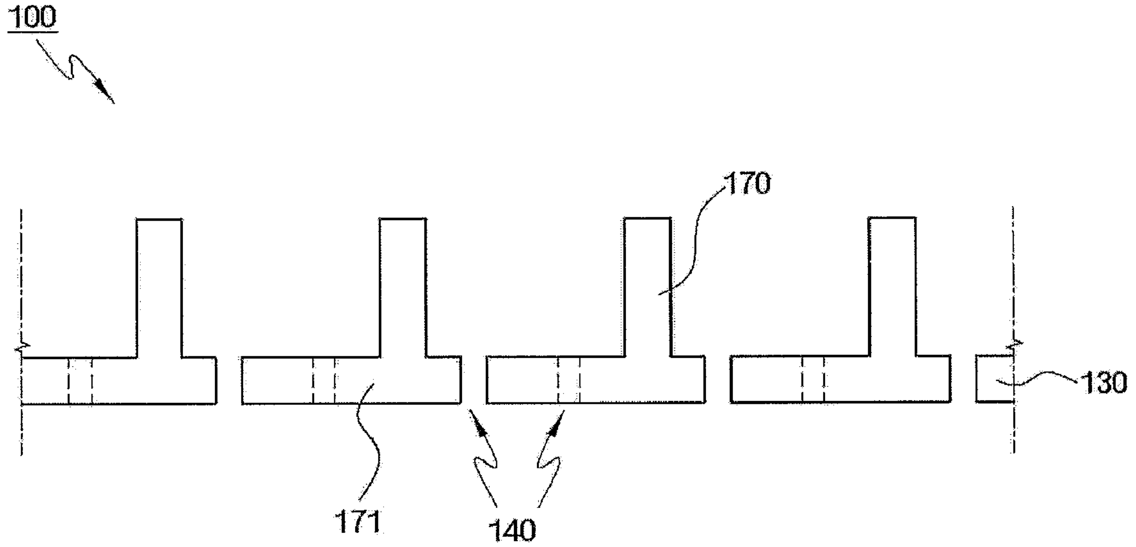
FIG. 26 is a sectional view of an intermediate structure for explaining a packaging method according to an embodiment of the present invention.

A packaging method according to an embodiment of the present invention will be described with reference to FIGS. 2 through 26. FIG. 26 is a sectional view of an intermediate structure for explaining a packaging method according to an embodiment of the present invention.

A method of fabricating a cover wafer 130 will now be described with reference to FIG. 26. A plurality of cover wafer protrusions 170 are formed on the cover wafer 130. The cover wafer protrusions 170 may be manufactured by forming a plurality of recesses on the cover wafer 130. The plurality of recesses may be formed by, for example, wet etching, dry etching, sand blast, or the like, but not limited thereto.

Subsequently, at least one inlet/outlet 140 shaped as a hole extending through the cover wafer 130 is formed in the cover wafer 130. The inlet/outlet 140 may be formed by, for example, wet etching, dry etching, sand blasting, or the like, but is not limited thereto.

Next, the cover wafer 130 having the plurality of cover wafer protrusions 170 and the inlet/outlet 140 is bonded to the support wafer 110 such that each of the cover wafer protrusions 170 corresponds to a biochip 120, thereby completing a wafer level package. The cover wafer 130 and the support wafer 110 may be bonded by, for example, anodic bonding, bonding using a sealant, or the like, but are not limited thereto.

Next, the wafer level package is cut to form spatially isolated reaction spaces RS. The wafers 110 and 130 can be cut through a sawing process, but are not limited thereto. The bonded wafers 110 and 130 are cut to form a plurality of biochip kits 300 having spatially isolated, discrete reaction spaces RS.

FIG. 26 illustrates the packaging method of the wafer level package 100 according to an embodiment of the present invention by way of example, but the method can be applied to the wafer level packages 101 and 102 according to other embodiments of the present invention.

The wafer level package can be fabricated by bonding a cover wafer to a support wafer on which biochips are integrated, thereby considerably simplifying the biochip kit manufacturing process. In addition, since the support wafer and the cover wafer are bonded to each other at an early stage, the biochips are not exposed, thereby efficiently preventing the biochips from being damaged.

A packaging method according to another embodiment of the present invention will now be described with reference to FIGS. 7 and 8.

First, the spacer wafer 150 having a plurality of openings 160 is bonded to the support wafer 110 on which a plurality of biochips 120 are integrated. The spacer wafer 150 includes a plurality of openings 160 shaped as holes extending through the spacer wafer 150. The openings 160 may be formed by, for example, punching, drilling, or the like, but are not limited thereto.

Subsequently, the spacer wafer 150 is bonded to the support wafer 110 such that the openings 160 correspond to the biochips 120. Even after the bonding of the spacer wafer 150, the biochips 120 on the support wafer 110 are exposed. The support wafer 110 and the spacer wafer 150 may be bonded by, for example, anodic bonding, bonding using a sealant, or the like, but are not limited thereto. The other characteristics of the spacer wafer 150 are the same as those described above.

Next, the cover wafer 130 is bonded to the spacer wafer 150 to define a reaction space RS formed by the support wafer 110, the spacer wafer 150 and the cover wafer 130. The cover wafer 130 may include a flat surface and a plurality of cover wafer protrusions (see 171 of FIG. 11). In embodiments in which the cover wafer 130 includes cover wafer protrusions, the cover wafer 130 is bonded to the spacer wafer 150, such that the cover wafer protrusions 171 correspond to the biochips 120 exposed through the spacer wafer 150. More specifically, the cover wafer 130 is bonded to the spacer wafer 150, such that the cover wafer protrusions 171 are aligned with the openings 160 formed on the spacer wafer 150. Likewise, the support wafer 110 may also include support wafer protrusions and may be bonded to the openings 160 of the spacer wafer 150.

Next, the bonded wafers 110, 150, and 130 are cut along the cutting line CL to form spatially isolated reaction spaces RS. This step is substantially the same as that in the packaging method according to the previous embodiment, and a detailed explanation will not be given.

While the packaging method has been described in the illustrated embodiment with regard to only the wafer level package 200 shown in FIG. 10, the method can also be applied to the wafer level packages 201, 202, 203, and 204 shown in FIGS. 11 through 14.

According to the packaging method according to another embodiment of the present invention, the biochip kit manufacturing process can be considerably simplified by forming a wafer level package. In addition, in embodiments in which the spacer wafer serves as an inlet/outlet, it is not necessary form a separate inlet/outlet in the cover wafer, thereby further simplifying the manufacturing process.

As described above, in wafer level packages according to some embodiments of the present invention, a reaction space is formed on a biochip by bonding the support wafer and the cover wafer, thereby simplifying the fabrication process, increasing the processing efficiency and reducing the manufacturing costs.

In wafer level packages according to other embodiments of the present invention, a spacer wafer is further provided between the support wafer and the cover wafer, e.g., so that a spatial margin for the reaction space can be provided, thereby enhancing the reaction efficiency. In addition, in embodiments in which the spacer wafer serves as an inlet/outlet, it is not necessary to form a separate inlet/outlet in the cover wafer, which greatly simplifies the manufacturing process, thereby improving the processing efficiency and reducing the costs.

In biochip kits according to some other embodiments of the present invention, since a cover is bonded to a substrate having biochips, the number of processing steps used to fabricate the biochip kits can be further reduced, which is advantageous from the viewpoints of the processing efficiency and the manufacturing costs.

In biochip kits according to other embodiments of the present invention, a spatial margin for the reaction space can be provided by a spacer provided between a substrate and a cover, thereby further enhancing the reaction efficiency. In addition, in embodiments in which the spacer serves as an inlet/outlet, it is possible to supply and exhaust a fluid without forming a separate inlet/outlet in the cover, thereby greatly simplifying the manufacturing process.

In wafer level packaging methods according to other embodiments of the present invention, wafer level packaging is enabled by bonding a cover wafer to a support wafer on which biochips are integrated, thereby considerably reducing the number of processing steps used to fabricate the biochip kits, which is advantageous from the viewpoints of the processing efficiency and the manufacturing costs. In addition, since the support wafer and the cover wafer are bonded to each other at an early stage, the biochips are not exposed to the environment, thereby efficiently preventing the biochips from being damaged.

In biochip kit packaging methods according to other embodiments of the present invention, since the biochip kits are manufactured using a wafer level package, the manufacturing process of the biochip kits can be simplified. In some embodiments, it is not necessary to form a separate inlet/outlet, thereby reducing the number of processing steps.

While the present invention has been particularly shown and described with reference to exemplary embodiments thereof, it will be understood by those of ordinary skill in the art that various changes in the form and details may be made therein without departing from the spirit and scope of the present invention as defined by the claims. It is therefore desired that the present embodiments be considered in all respects as illustrative and not restrictive, reference being made to the claims rather than the foregoing description to indicate the scope of the invention.

What is claimed is:

1. A package comprising:

a support on which a plurality of biochips are disposed; and a cover bonded to the support and defining a reaction space for each of the plurality of biochips together with the support, the cover including at least one inlet/outlet, wherein the reaction space includes a top surface, a bottom surface, and sidewalls, the top surface of the reaction space is formed by the cover, the bottom surface of the reaction space is formed by the support, and the sidewalls of the reaction space are formed by a combination of the support and the cover.

2. The package of claim 1, wherein the biochips include a plurality of active regions and a plurality of probes coupled to the active regions, the active regions being on a surface of the support.

3. A package comprising:

a support on which a plurality of biochips are disposed;

a spacer bonded to the support and having a plurality of openings corresponding to the plurality of biochips, each of the plurality of openings exposing a biochip, wherein the spacer comprises an inlet/outlet; and a cover bonded to the spacer and defining a reaction space for each of the plurality of biochips together with the support and the spacer.

4. The package of claim 3, wherein the spacer comprises silicone or urethane.

5. The package of claim 3, wherein the spacer comprises a self-sealing material.

6. The package of claim 3, wherein the reaction space includes a top surface, a bottom surface, and sidewalls, the top surface of the reaction space is formed by the cover, the bottom surface of the reaction space is formed by the support, and the sidewalls of the reaction space are formed by the support alone, the cover alone, the spacer alone, or a combination of the support, the spacer and the cover.

7. The package of claim 3, wherein the cover includes at least one inlet/outlet.

8. The package of claim 3, wherein the biochips include a plurality of active regions and a plurality of probes coupled to the active regions, the active regions being on a surface of the support.

9. A biochip kit comprising:

a substrate on which a biochip is disposed; and a cover bonded to the substrate and defining a reaction space over the biochip together with the substrate, the cover including at least one inlet/outlet, wherein the reaction space includes a top surface, a bottom surface, and sidewalls, the top surface of the reaction space is formed by the cover, the bottom surface of the reaction space is formed by the substrate, and the sidewalls of the reaction space are formed by a combination of the substrate and the cover.

10. The biochip kit of claim 9, wherein the biochip includes a plurality of active regions and a plurality of probes coupled to the active regions, the active regions being on the substrate.

11. The biochip kit of claim 9, wherein the substrate includes a substrate protrusion and the cover includes a cover protrusion, the cover protrusion corresponding to the substrate protrusion.

12. A biochip kit comprising:

a substrate on which a biochip is disposed;

a spacer bonded to the substrate and having an opening corresponding to the biochip, the opening exposing the biochip, wherein the spacer comprises an inlet/outlet; and a cover bonded to the spacer and defining a reaction space over the biochip together with the substrate and the spacer, the cover including at least one inlet/outlet.

13. The biochip kit of claim 12, wherein the spacer comprises silicone or urethane.

14. The biochip kit of claim 12, wherein the spacer comprises a self-sealing material.

15. The biochip kit of claim 12, wherein the reaction space includes a top surface, a bottom surface, and sidewalls, the top surface of the reaction space is formed by the cover, the bottom surface of the reaction space is formed by the substrate, and the sidewalls of the reaction space are formed by the spacer alone, a combination of the spacer and the cover, or a combination of the spacer and the substrate.

16. The biochip kit of claim 12, wherein the cover includes at least one inlet/outlet.

17. The biochip kit of claim 12, wherein the cover includes a cover protrusion corresponding to the biochip.

18. The biochip kit of claim 12, wherein the substrate includes a substrate protrusion and the cover includes a cover protrusion, the cover protrusion and the substrate protrusion facing each other.

19. A packaging method comprising:

providing a support on which a plurality of biochips are disposed; and bonding a cover to the support to form a package, the cover including at least one inlet/outlet and defining a reaction space for each of the plurality of biochips together with the support, wherein the cover includes a plurality of cover protrusions, each corresponding to each of the plurality of biochips and wherein the reaction space includes a top surface, a bottom surface, and sidewalls, the cover protrusions being sidewalls of the reaction space.

20. The packaging method of claim 19, wherein the bonding of the cover to the support comprises bonding the cover to the support including a plurality of support protrusions, the support protrusions corresponding to the cover protrusions.

21. A biochip kit packaging method comprising:

providing a support on which a plurality of biochips are disposed;

bonding a cover to the support to form a package, the cover including at least one inlet/outlet and defining a reaction space for each of the plurality of biochips together with the support; and cutting the package to separate the plurality of biochips, each biochip having a discrete reaction space.

22. A packaging method comprising:

providing a support on which a plurality of biochips are disposed;

bonding a spacer having a plurality of openings corresponding to the plurality of biochips, each of the plurality of openings exposing each of the plurality of biochips, the spacer being inlet/outlet; and bonding a cover to the spacer to form a package, the cover defining a reaction space for each of the plurality of biochips together with the support and the spacer.

23. The packaging method of claim 22, wherein the spacer comprises silicone or urethane.

24. The packaging method of claim 22, wherein the spacer comprises a self-sealing material.

25. The wafer level packaging method of claim 22, wherein the cover includes at least one inlet/outlet.

26. A biochip kit packaging method comprising:

providing a support on which a plurality of biochips are disposed bonding a spacer having a plurality of openings corresponding to the plurality of biochips, each of the plurality of openings exposing each of the plurality of biochips;

bonding a cover to the spacer to form a package, the cover defining a reaction space for each of the plurality of biochips together with the support and the spacer; and cutting the package to separate the plurality of biochips, each biochip having a discrete reaction space.

27. The biochip kit packaging method of claim 26, wherein the spacer comprises silicone or urethane.

28. The biochip kit packaging method of claim 26, wherein the spacer comprises a self-sealing material.

29. The biochip kit packaging method of claim 26, wherein the cover includes at least one inlet/outlet.

* * * * *